(12) United States Patent
Hutchinson (10) Patent No.: US 8,984,959 B2
(45) Date of Patent: Mar. 24, 2015

(54) STEAM QUALITY AND FLOW RATE MEASUREMENT SYSTEM

(71) Applicant: Dan Hutchinson, Denver, CO (US)

(72) Inventor: Dan Hutchinson, Denver, CO (US)

( * ) Notice: Subject to any disclaimer, the term of this patent is extended or adjusted under 35 U.S.C. 154(b) by 221 days.

(21) Appl. No.: 13/866,198

(22) Filed: Apr. 19, 2013

(65) Prior Publication Data

US 2014/0311251 A1    Oct. 23, 2014

(51) Int. Cl.
*G01N 27/22* (2006.01)
*G01N 25/60* (2006.01)

(52) U.S. Cl.
CPC .............. *G01N 27/226* (2013.01); *G01N 25/60* (2013.01)
USPC ..................................................... 73/861.04

(58) Field of Classification Search
CPC ............. G01F 1/74; G01F 15/08; G01F 1/58; G01F 1/44
See application file for complete search history.

(56) References Cited

U.S. PATENT DOCUMENTS

| | | | | |
|---|---|---|---|---|
| 4,149,403 A | * | 4/1979 | Muldary et al. | 73/29.03 |
| 4,832,503 A | | 5/1989 | Dowling et al. | |
| 4,849,687 A | | 7/1989 | Sims et al. | |
| 4,854,725 A | | 8/1989 | Sims et al. | |
| 5,190,105 A | * | 3/1993 | D'Souza | 166/303 |
| 5,307,833 A | * | 5/1994 | Stoy et al. | 137/118.04 |
| 5,869,771 A | * | 2/1999 | Rajan et al. | 73/861.04 |
| 6,412,351 B1 | * | 7/2002 | Zunft | 73/861.04 |
| 2002/0139197 A1 | * | 10/2002 | Salamitou et al. | 73/861.04 |
| 2003/0074982 A1 | * | 4/2003 | Spielman | 73/861.63 |
| 2004/0221660 A1 | * | 11/2004 | Dutton et al. | 73/861.354 |

OTHER PUBLICATIONS

J.C. Sims and D.H. Huthcinson, The Dielectric Steam Quality Sensor Laboratory Development and Field Evaluation, Society of Petroleum Engineers, 1997, pp. 23-35, SPE 37514, Society of Petroleum Engineers, US.
Suzanne Griston and Dan Hutchinson, Field Testing of Dielectric Steam Quality Sensor, Society of Petroleum Engineers, 1998, 12 pages, SPE 46236, Society of Petroleum Engineers, US.
Suzanne Castrup and Faisal Latif and Ali Al Kalbani, Tapered-Bean Steam Chokes Revisited, Society of Petroleum Engineers, 2011, 8 pages, SPE 144615-PP, Society of Petroleum Engineers, US.
Sze-Foo Chien, Predicting Wet-Steam Flow Regime in Horizontal Pipes, Journal of Petroleum Technology, Mar. 1990, pp. 356-362, Journal of Petroleum Technology, US.

* cited by examiner

*Primary Examiner* — Jewel V Thompson
(74) *Attorney, Agent, or Firm* — Leyendecker and Lemire, LLC (57) ABSTRACT

A steam quality and flow rate measurement system is described. Embodiments of the system include a steam quality measuring device having a converging/diverging nozzle and ceramic spacer. The steam quality measuring device can be adapted to measure an impedance of a two-phase steam to determine steam quality. The converging/diverging nozzle can be implemented to mix the two-phase flow and reduce pressure loss. The ceramic spacer can be positioned such that steam is in a cross flow when interfacing with the ceramic spacer inside the steam quality measuring device. By placing the spacer in such a position, an electrically conductive liquid phase can be prevented from coating a surface of the ceramic spacer.

20 Claims, 6 Drawing Sheets

STEAM QUALITY AND FLOW RATE MEASUREMENT SYSTEM

BACKGROUND

Knowing or predicting multi-phase conditions for wet steam flowing in a steam-distributing network is important to the engineering, management, and economics of steamflood enhanced oil recovery (EOR). All steam EOR systems involve a steam distribution system. Most steams used in oil field steam operations are "saturated" or "wet steam". More specifically, the steam can be classified as a two-phase flow including steam vapor and liquid water. The proportion of each phase at a point in the distributions system can be affected by frictional pressure loss, liquid holdup, and unequal phase mixtures exiting piping junctions. Phase splitting occurs when liquid water separates from the steam. The two phases have very different properties, including energy content. Defining the amount of each phase delivered to any point of consumption is important to the efficient and effective operation of oil recovery projects.

One way of determining the amount of each phase in two phase steam flow is to measure steam quality. Steam quality can be defined as the ratio of the vapor phase flow rate divided by the total flow rate (vapor plus water). Previously known methods of measuring steam quality include using a dielectric steam quality sensor (DSQS). A DSQS measures an electrical impedance of a two-phase steam flowing through a region between two conductors. Using measurements from the DSQS, a flow engineer can determine steam quality. By determining the steam quality in a given enhanced oil recovery system, the flow engineer can maximize the effectiveness of the steam introduced to an oil well.

The extent and nature of mixing of the two phases, or "flow regime" is critical to the function of impedance sensing devices. However, the flow regime of two-phase flows can be unpredictable and, thereby, produce inaccurate measurements. Uncontrolled flow regime is one factor that can lead to inaccurate results when using a DSQS. In some instances, liquid phase forms a direct electrical connection between electrodes and/or conductive films, on one or more of the electrical insulating components, producing inaccurate measurements.

DETAILED DESCRIPTION

Embodiments of the present invention include a multi-phase steam quality and flow rate measurement system. The system can include a steam quality measuring device coupled to a steam generator and one or more injectors. The steam quality measuring device can be implemented to control flow rate and determine steam quality in an enhanced oil recovery system.

Embodiments of the steam quality measuring device can include a housing assembly, an electrode mounting assembly, and a phase mixing nozzle. Generally, the housing assembly includes a pipe having multiple openings or orifices each adapted for a specific purpose. For instance, two of the openings can be adapted to receive a two-phase flow into and out of the device, another opening can be adapted to receive the electrode mounting assembly, and another opening can be adapted to receive the phase mixing nozzle.

Generally, the steam quality measuring device can be adapted to form a capacitance sensor. The pipe can be used as one of two electrical conductors in the capacitance sensor. The electrode assembly can include an electrode that can be implemented as the other electrical conductor in the capacitance sensor.

The phase mixing nozzle can be implemented to create two-phase flow regimes with zero slip, and vapor continuous phase, by intimately mixing the two-phase flow. A zero slip flow regime generally provides an accurate determination of an amount of vapor phase and liquid phase in steam. The vapor continuous phase can provide a medium which can allow consistent capacitance measurement. In an embodiment, the phase mixing nozzle can be located approximate the electrode in the steam quality measuring device. The mixed flow condition exiting the mixing nozzle can be maintained and directed toward the electrode and into a void created between the electrode and the pipe. The two-phase steam mixture can constitute a dielectric between the two conductor elements of the capacitance sensor. Steam quality can be interpreted from a measured impedance of the two-phase steam.

Some embodiments of the measuring device can include an electrically insulative spacer with controlled dielectric properties. The spacer can be adapted to support an inner electrode of the capacitance sensor. In one embodiment, the spacer can be positioned such that steam is in a cross flow when interfacing with the spacer. By placing the spacer in such a position, an electrically conductive liquid phase can be prevented from coating a surface of the spacer.

Pressure and/or temperature sensors can be implemented to define conditions upstream and downstream of the mixing nozzle. The measured conditions associated with the mixed flow can be used to calculate the steam quality and flow rate. A pressure loss across a specific mixing nozzle design, combined with the steam quality, can enable a determination of total flow rate. In some embodiments, with consideration of operating conditions, the mixing nozzle can be configured to control the steam flow rate.

TERMINOLOGY

The terms and phrases as indicated in quotation marks (" ") in this section are intended to have the meaning ascribed to them in this Terminology section applied to them throughout this document, including in the claims, unless clearly indicated otherwise in context. Further, as applicable, the stated definitions are to apply, regardless of the word or phrase's case, to the singular and plural variations of the defined word or phrase.

The term "or" as used in this specification and the appended claims is not meant to be exclusive; rather the term is inclusive, meaning either or both.

References in the specification to "one embodiment", "an embodiment", "another embodiment, "a preferred embodiment", "an alternative embodiment", "one variation", "a variation" and similar phrases mean that a particular feature, structure, or characteristic described in connection with the embodiment or variation, is included in at least an embodiment or variation of the invention. The phrase "in one embodiment", "in one variation" or similar phrases, as used in various places in the specification, are not necessarily meant to refer to the same embodiment or the same variation.

The term "couple" or "coupled" as used in this specification and appended claims refers to an indirect or direct physical connection between the identified elements, components, or objects. Often the manner of the coupling will be related specifically to the manner in which the two coupled elements interact.

The term "directly coupled" or "coupled directly," as used in this specification and appended claims, refers to a physical connection between identified elements, components, or objects, in which no other element, component, or object resides between those identified as being directly coupled.

The term "approximately," as used in this specification and appended claims, refers to plus or minus 10% of the value given.

The term "about," as used in this specification and appended claims, refers to plus or minus 20% of the value given.

The terms "generally" and "substantially," as used in this specification and appended claims, mean mostly, or for the most part.

Directional and/or relationary terms such as, but not limited to, left, right, nadir, apex, top, bottom, upstream, downstream, vertical, horizontal, back, front and lateral are relative to each other and are dependent on the specific orientation of a applicable element or article, and are used accordingly to aid in the description of the various embodiments and are not necessarily intended to be construed as limiting.

The term "software," as used in this specification and the appended claims, refers to programs, procedures, rules, instructions, and any associated documentation pertaining to the operation of a system.

The term "firmware," as used in this specification and the appended claims, refers to computer programs, procedures, rules, instructions, and any associated documentation contained permanently in a hardware device and can also be flashware.

The term "hardware," as used in this specification and the appended claims, refers to the physical, electrical, and mechanical parts of a system.

The terms "computer-usable medium" or "computer-readable medium," as used in this specification and the appended claims, refers to any medium that can contain, store, communicate, propagate, or transport the program for use by or in connection with the instruction execution system, apparatus, or device. The computer-usable or computer-readable medium may be, for example but not limited to, an electronic, magnetic, optical, electromagnetic, infrared, or semiconductor system, apparatus, device, or propagation medium. By way of example, and not limitation, computer readable media may comprise computer storage media and communication media.

The term "signal," as used in this specification and the appended claims, refers to a signal that has one or more of its characteristics set or changed in such a manner as to encode information in the signal. It is to be appreciated that wireless means of sending signals can be implemented including, but not limited to, Bluetooth, Wi-Fi, acoustic, RF, infrared and other wireless means.

An Embodiment of a Steam Quality Measurement System

Figure 1:
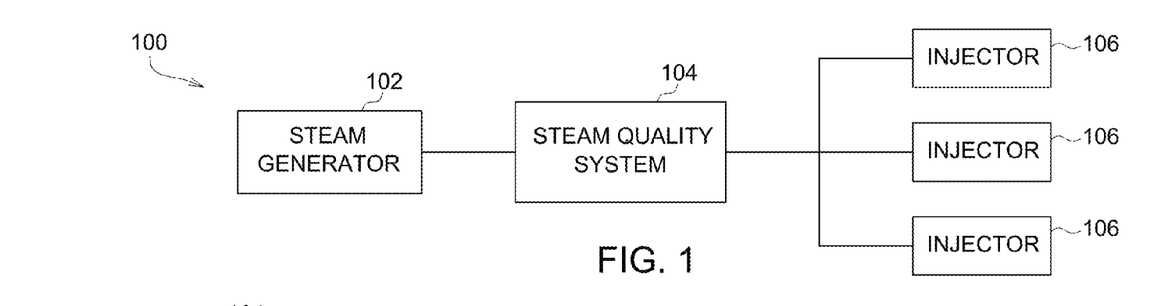
FIG. 1 is a block diagram of an enhanced oil recovery system according to one embodiment of the present invention.

Referring to FIG. 1, a block diagram of an embodiment 100 showing an enhanced oil recovery system is illustrated. The enhanced oil recovery system 100 includes means of thermally affecting an oil reserve. By thermally affecting the oil reserve, a higher percentage of oil recovery can be achieved in some instances.

Generally, the enhanced oil recovery system 100 includes a steam generator 102, a steam quality system 104, and one or more injectors 106 adapted to deliver steam to an oil reserve. In one embodiment, the steam generator 102 can be powered by fossil fuels. It is to be appreciated that other means of generating steam can be implemented including, but not limited to, solar powered steam generators.

Steam generated by the steam generator 102 can be channeled to the steam quality system 104 before being routed to the injectors 106 to be delivered to an oil reserve. The steam quality system 104 can be configured to collect data used to determine the quality of the steam generated by the steam generator 102. In one embodiment, data measured by the steam quality system 104 can be used by an engineer to determine how to control an overall flow rate of the system 100.

Figure 2:
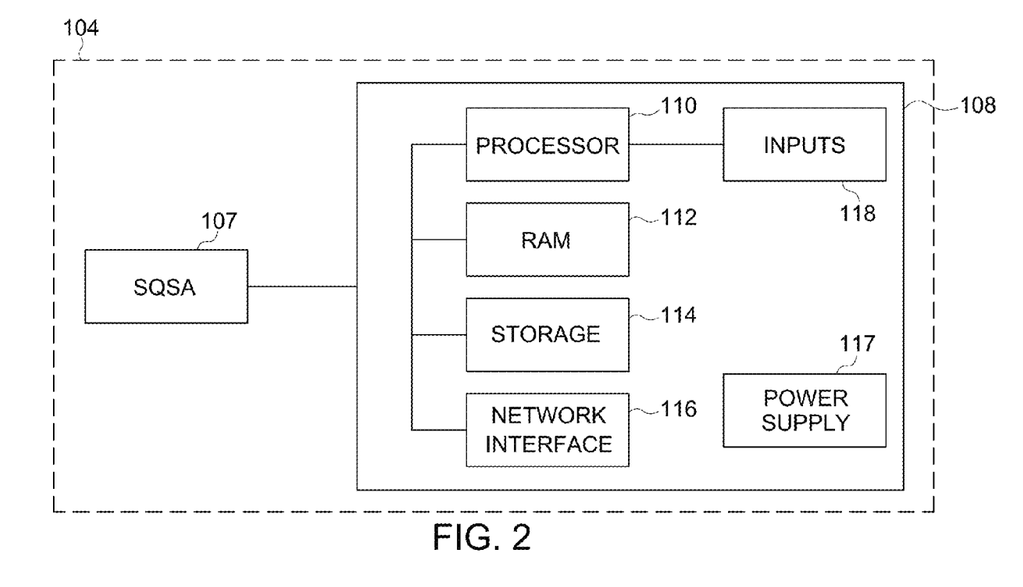
FIG. 2 is block diagram of a steam quality system according to one embodiment of the present invention.

Referring to FIG. 2, a block diagram of the steam quality system 104 is shown. Generally, the steam quality system 104 includes a steam quality sensor assembly 107 and a control module 108.

The control module 108 can include a processor 110, a random access memory 112, and a nonvolatile storage 114 (or memory), as shown in FIG. 2. The processor 110 can be a single microprocessor, multi-core processor, or a group of processors. The random access memory 112 can store executable code as well as data that may be immediately accessible to the processor 110, while the nonvolatile storage 114 can store executable code and data in a persistent state.

The control module 108 can also include a network interface 116. The network interface 116 can include hardwired and wireless interfaces through which the control module 108 can communicate with other devices. For example, the control module 108 can wirelessly interface with a computing device used by an oil field engineer. In another example, the control module 108 can wirelessly interface with one or more sensors of the steam quality sensor assembly 107.

Generally, the controller can include a power supply 117. In one embodiment, the power supply 117 can be a battery charged by converted solar energy. It is to be appreciated that other means of powering the control module 108 can be implemented. For instance, a pre-charged battery can be implemented to power the control module 108.

One or more inputs 118 can be included as part of the control module 108 to receive signals from sensors associated with the steam quality sensor assembly 107. For example, a pressure sensor in the steam quality sensor assembly 107 can send pressure readings via a signal to the control module 108. Some embodiments of the present invention can include a wireless interface between the control module 108 and various sensors.

The controller 108 can be adapted to calculate a steam quality based on information received from the steam quality sensor assembly 107. For example, based on signals received from the sensors including a capacitance sensor, the controller 108 can calculate or measure steam quality. In one embodiment, the network interface 116 can send a signal containing the calculated steam quality to a remote location. For instance, a real-time steam quality measurement can be sent to an engineer in charge of overseeing the enhanced oil recovery system 100. In another embodiment, the memory 114 can be adapted to store real time steam quality measurements for later retrieval by an engineer.

The measured impedance of the two-phase flow can be correlated with a volume fraction of each phase, and further interpreted as steam quality. Pressure and/or temperature sensors can be used to define process conditions in the steam quality sensor assembly 107. Properties of saturated vapor and liquid phase upstream and downstream of a nozzle in the steam quality sensor assembly 107 can be used to calculate steam quality and flow rate. Total flow rate can be calculated based on steam quality and a pressure loss across the steam quality sensor assembly 107.

Figure 3:
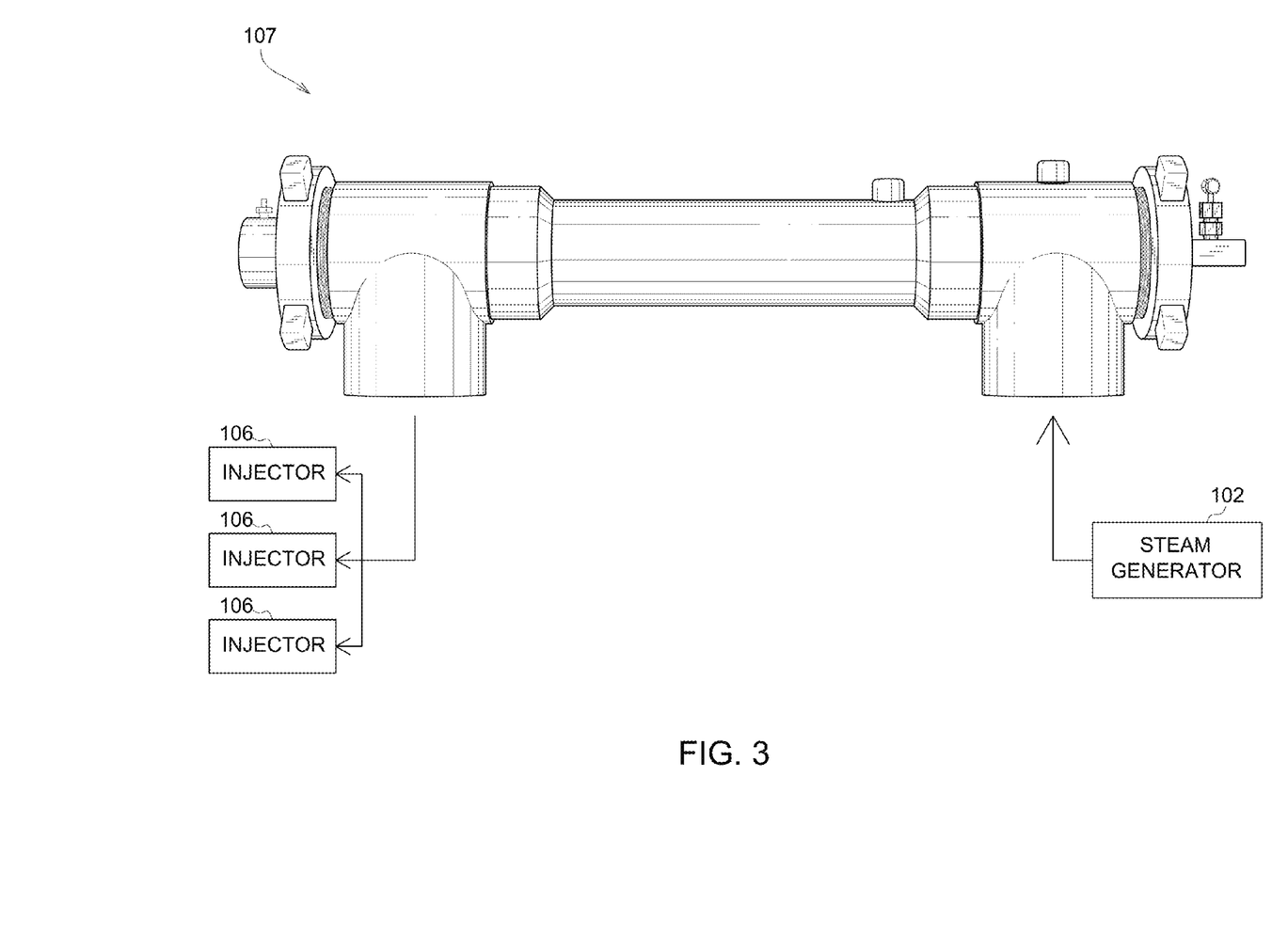
FIG. 3 is a side view of a steam quality measurement device according to one embodiment of the present invention.

Referring to FIG. 3, a detailed diagram of a steam quality sensor assembly 107 is illustrated. As shown, the steam quality sensor assembly 107 has an orifice adapted to receive steam from the steam generator 102. As steam passes through the steam quality sensor assembly 107, the steam can exit via another orifice and continue on to the injectors 106. In one embodiment, all steam generated by the steam generator 102 can be channeled to the steam quality sensor assembly 107 and then on to the injectors 106. It is to be appreciated that less than 100% of steam generated by the steam generator 102 can be channeled through the steam quality system 104 for testing steam quality. For example, 20% of steam generated can be channeled through the steam quality system 104 for testing purposes.

Figure 4:
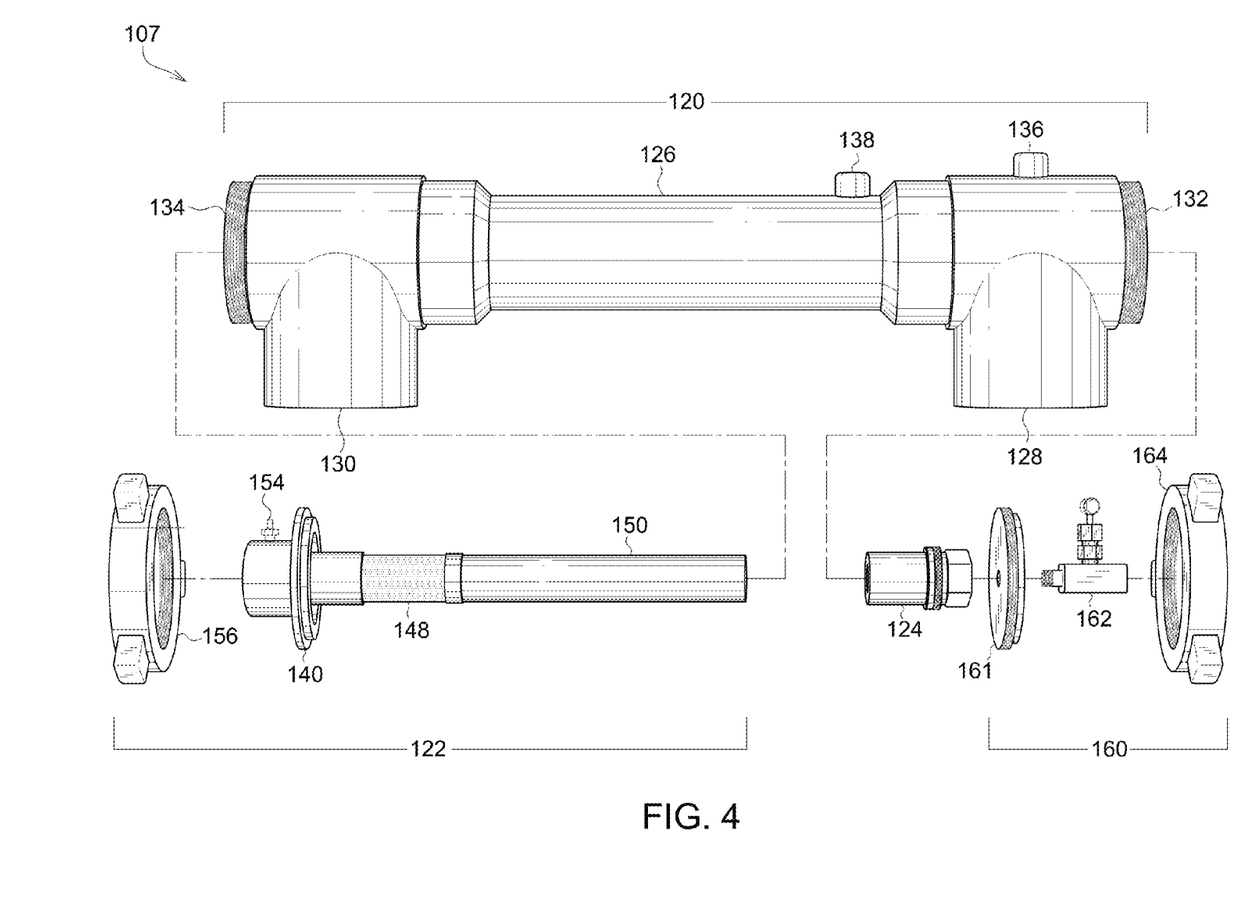
FIG. 4 is an exploded view of a steam quality measurement device according to one embodiment of the present invention.

Referring to FIG. 4, an exploded view of the steam quality sensor assembly 107 is illustrated. Generally, the sensor assembly 107 includes a housing assembly 120, an electrode mounting assembly 122, a nozzle 124, and a pressure release assembly 160.

As shown, the housing assembly 120 can include a pipe 126 having a first opening 128, a second opening 130, a third opening 132, and a fourth opening 134. The first opening 128 and the second opening 130 can be located approximate ends of the pipe 124. In one embodiment, the first opening 128 and the second opening 130 can be orthogonal to the pipe 126. The third opening 132 and the fourth opening 134 can be located at opposite ends of the pipe 126, as shown in FIG. 4. In one embodiment, the third opening 132 can be adapted to receive the nozzle 124 and the pressure release assembly 160 and the fourth opening 134 can be adapted to receive the electrode mounting assembly 122.

In one embodiment, the first opening 128 can be an inlet port and the second opening 130 can be an outlet port. The inlet port 128 can be adapted to receive steam from the steam generator 102 and direct steam through the pipe 126 towards the electrode mounting assembly 122. The outlet port 130 can be adapted to direct steam out of the pipe 126. Generally, the inlet port 128 and the outlet port 130 can extend orthogonally away from the pipe 126. Depending on an implementation, the length of each port can be increased or decreased. In one embodiment, the inlet port 128 and the outlet port 130 can each be threaded. In another embodiment, the inlet port 128 and the outlet port 130 can have flanged connections. It is to be appreciated that other means of connecting the ports to piping of the enhanced oil recovery system 100 can be implemented.

Figure 5:
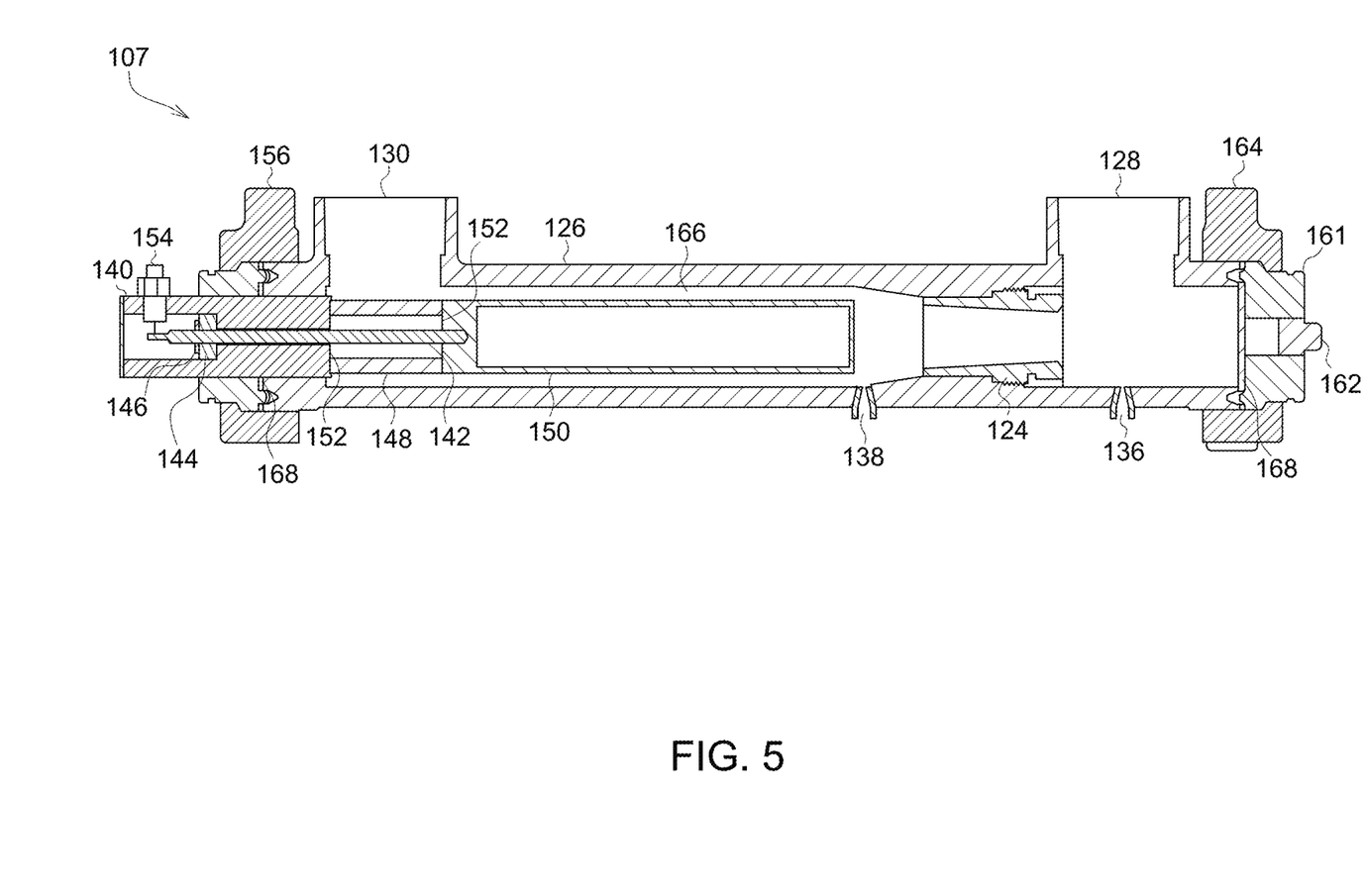
FIG. 5 is a cross-sectional view of a steam quality measurement device according to one embodiment of the present invention.

In some embodiments, the pipe 126 can include a fifth opening 136 and a sixth 138 opening. Generally, the fifth opening 136 is located upstream of the nozzle 124 and the sixth opening 138 is located downstream of the nozzle 124, as shown in FIG. 5. The fifth opening 136 and the sixth opening 138 can be adapted to receive and couple to one or more sensors. For instance, the fifth opening 136 can couple to a pressure sensor and the sixth opening 138 can couple to a temperature sensor. In another instance, the fifth opening 136 can couple to a temperature sensor and the sixth opening 138 can couple to a pressure sensor. It is to be appreciated that other types of sensors can be implemented in the present invention.

Referring to FIG. 5, a cross-sectional view of the steam quality sensor assembly 107 is illustrated. As shown in FIGS. 4 and 5, the electrode mounting assembly 122 can include a mounting 140, a rod 142, a first insulator 144, a tensioning block 146, a second insulator 148, an electrode 150, one or more seals 152, and an electronic connector 154. An end cap 156 can be implemented to couple the electrode mounting assembly 122 to the pipe 126.

In one embodiment, the mounting 140 can be a machined from a rigid material. The mounting 140 can be adapted to couple components of the electrode mounting assembly 122 to the end cap 156. Generally, the mounting 140 can directly couple to the end cap 156 and the end cap 156 can directly couple to the housing assembly 120. For instance, an outer threading of the mounting 140 can threadably engage an inner threaded portion of the end cap 156. It is to be appreciated that other means of coupling the mounting 140 to the end cap 156 can be implemented in the present invention.

Generally, the end cap 156 can be removably coupled to the housing assembly 120. For instance, the end cap 156 can be removably coupled approximate the fourth opening 134 of the housing assembly 120, as shown in FIG. 4.

Generally, the rod 142 can be comprised of an electrically conductive material. In one embodiment, the conductive rod 142 can be coupled to the electrode 150. To provide an electrical charge to the electrode 150, the conductive rod 142 can be electrically connected to the electronic connector 154. In one embodiment, the conductive rod 142 can be electrically isolated from the pipe 126.

As shown in FIG. 5, the first insulator 144 can be included to position the conductive rod 142 and electrically isolate the conductive rod 142 from the mounting 140 and the pipe 126. In one embodiment, the first insulator 144 can be comprised of an electrically insulating material. For instance, materials from which the first insulator 144 can be made from include, but are not limited to, machinable ceramics and/or other materials with high compressive strength, low electrical conductivity, a low dielectric constant, and stability of all mentioned properties at elevated temperatures.

The tensioning block 146 can include, but is not limited to, a threaded retaining block, a clamping device, and/or a nut. The tensioning nut 146 can be adapted to couple the conductive rod 142 to the electrode 150. For example, the tensioning nut 146 can mechanically secure the conductive rod 142 and the electrode 150 by compressive forces. The compressive forces can be created by tightening the tensioning nut 146 and can be applied to the conductive rod 142 and the first insulator 144.

The second insulator 148 can be included as a spacer between the mounting 140 and the electrode 150. In one embodiment, the spacer 148 can be a tube adapted to receive and insulate the conductive rod 142, as shown in FIG. 5. Generally, the spacer 148 can be comprised of a ceramic material having electrically insulating properties. For example, the spacer 148 can comprise a silicon carbide ceramic. In another example, the spacer 148 can comprise a silicon nitride ceramic. Generally, the spacer 148 can be selected from materials having ultra-low silicate content and corrosion resistance to high temperature and high pH conditions. It is to be appreciated that materials with high compressive strength, low electrical conductivity, a low dielectric constant, and stability of all properties at elevated temperatures can be implemented in the present invention.

In one embodiment, the spacer 148 can be located approximate the outlet port 130. With the outlet port 130 orthogonally oriented to a longitudinal axis of the housing assembly 120, steam flow can generally be transverse to a longitudinal axis of the spacer 148. The transverse flow near the spacer 148 can prevent accumulation of electrically conductive liquid films on a surface of the spacer 148.

Generally, the seals 152 can be adapted to prevent steam from entering into an interior of the spacer 148. In one embodiment, the seals 152 can be located at an interface between the spacer 148 and the mounting 140 and the spacer 148 and the electrode 150. For instance, the seals 152 can interface with both ends of the spacer 148 and with the mounting 140 and the electrode 150.

Generally, the electronic connecter 154 can be coupled to the power supply 117. The power supply 117 can provide an electrical charge to the electronic connector 154. The electronic connector 154 can be adapted to create an electrical connection to the conductive rod 142 and the housing assembly 120. The electrode 150 can be coupled to the electronic connector 154 via the conductive rod 142. In one embodiment, the electrical connection to the housing assembly 120 and the conductive rod 142 can be electrically isolated from each other. As such, the housing assembly 120 and the electrode 150 can form a capacitor where the steam acts as a dielectric.

As shown in FIG. 5, when the electrode mounting assembly 122 is inserted into the pipe 124, a void 166 can be created between an interior of the pipe 124 and the electrode mounting assembly 122. In one embodiment, the void 166 can be an annular void. The annular void 166 can be used to calculate a steam quality. Two-phase flow filling the annular void 166 of the pipe 124 can conduct electricity between the electrode 150 and the pipe 124 and act as a dielectric in a capacitor.

In some embodiments, the sensor assembly 107 can include the pressure release assembly 160. The pressure release assembly 160 can include a mounting 161 and a device 162 adapted to control release of steam pressure inside the housing assembly 120. For example, the pressure release device 162 can include, but is not limited to, a threaded relief plug, a valve, and/or other devices adapted to vent or release steam pressure. The pressure release device 162 can couple to the mounting 161. For example, the pressure release device 162 can be threadably engaged with the mounting 161. The pressure release device 162 can be coupled to an end cap 164 via the mounting 161. The end cap 164 can be removably coupled to the housing assembly 120. Generally, the end cap 164 is removably coupled approximate the third opening 132 of the housing assembly 120.

The pressure release end cap 164 and the electrode end cap 156 can each include a seal 168. In one embodiment, the seal 168 can be a high temperature pressure seal or gasket. The seal 168 can be adapted to sustain repeated removal and replacement of the end caps 156 and 164. For instance, the seal 168 can be adapted to facilitate an initial installation of the nozzle 124 and subsequent removal, resizing, and replacement of the nozzle 124 to accommodate changes in the enhanced oil recovery system 100 evolving over a life of the system.

Figure 6A:
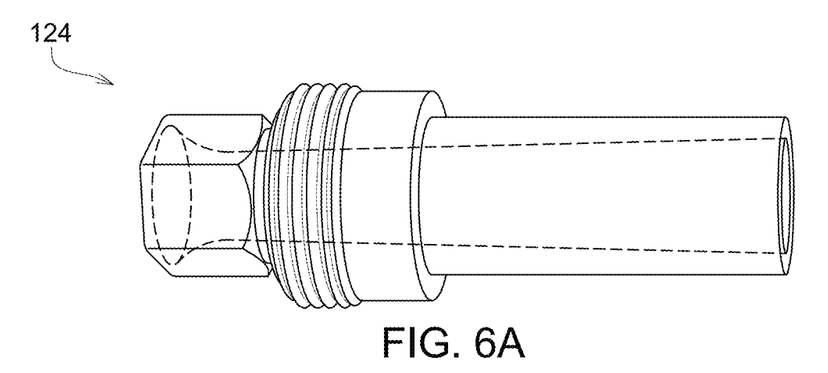
FIG. 6A is a side view of a nozzle according to one embodiment of the present invention.
Figure 6B:
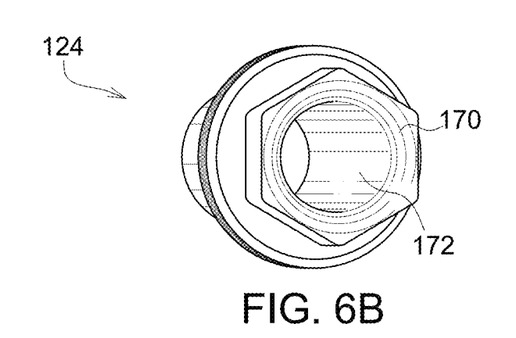
FIG. 6B is a top view of a nozzle according to one embodiment of the present invention.
Figure 6C:
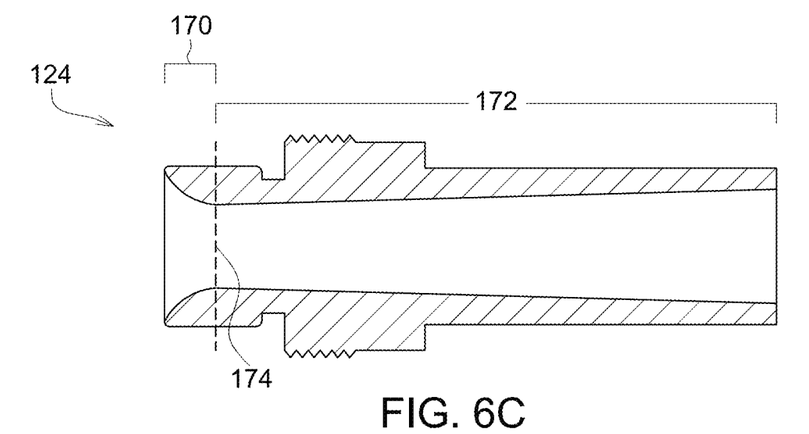
FIG. 6C is a cross-sectional view of a nozzle according to one embodiment of the present invention.

Referring to FIGS. 6A-6C, detailed diagrams of one embodiment of the nozzle 124 are shown. FIG. 6A is a side view of one embodiment of the nozzle 124 showing the interior bore converging and diverging. FIG. 6B is a top view of the nozzle 124 showing a converging portion of the nozzle 124. FIG. 6C is a cross-sectional view of the nozzle 124.

Generally, the nozzle 124 can be implemented to create a hydraulic flow condition which can intimately mix a liquid phase and a vapor phase of steam. The nozzle 124 can create a flow regime condition characterized by a continuous vapor phase and a liquid phase completely suspended in the vapor phase, commonly known as mist phase flow regime, droplet flow, aerosol flow, and/or other terminology which implies a continuous vapor phase and intimately mixed liquid phase completely suspended in the vapor phase. The mixed flow condition created by the nozzle 124 can be maintained through the pipe 126 and thereby can enable an accurate impedance measurement of the two-phase steam.

In one embodiment, the nozzle 124 can be a converging/diverging nozzle or de Laval nozzle. The converging/diverging nozzle 124 can produce optimum mixing characteristics with minimal pressure loss. It is to be appreciated that the nozzle 124 can be a constant bore choke or nozzle, or other flow restricting device sized and shaped to create a desired mixing of the two-phase flow, as specified herein.

In addition to mixing, measurement of a pressure drop across the nozzle 124 can be combined with a steam quality measurement to compute a mass flow rate of the two-phase steam, and a total steam mass flow rate. Generally, a pressure drop across the nozzle 124 of up to 15% can be acceptable and allows for flow measurement. It is to be appreciated that greater pressure drops can allow for flow rate control. In one embodiment, a pressure drop of at most 10% can be acceptable. It is to be appreciated that the pressure drop can be increased or decreased depending on certain conditions of the enhanced oil recovery system 100.

As shown in FIG. 5, an internal diameter of the nozzle 124 diverges or increases as the two-phase steam flows downstream towards the electrode 150. In one embodiment, the diameter of the nozzle 124 can reach an interior diameter of the pipe 126 prior to the electrode 150. By converging and then quickly diverging the bore of the nozzle 124, the nozzle 124 can mix the two-phase flow to generate a vapor continuous flow regime and to recover pressure loss by converting kinetic energy back to potential energy.

As shown in FIG. 6C, a converging portion 170 of the converging/diverging nozzle 124 can be upstream of a diverging portion 172. A throat 174 of the nozzle 124 is generally located approximate an end having the converging portion 170. The throat 174 can be a portion of the nozzle 124 with the smallest cross-section (or diameter). The throat 174 can be located approximate where the nozzle 124 changes from converging to diverging. Generally, the converging portion 170 is smaller in length than the diverging portion 172 relative an overall length of the nozzle 124. For example, for a nozzle having a 4 inch length, the converging portion can be a ¼ of an inch long and the diverging portion can be 3 and ¾ of an inch long. It is to be appreciated that the size or length of the converging portion 170 and the diverging portion 172 can be altered.

In one embodiment, a length of the nozzle 124 can be four inches. In another embodiment, the length of the nozzle 124 can be three inches. It is to be appreciated that a length of the nozzle 124 can be varied depending on a specific implementation and requirement of an enhanced oil recovery system.

A diameter of the throat 174 can be adjusted based on a specific implementation of the nozzle 124. For example, a diameter of the throat can vary from three-eighths of an inch (0.375") to one and three-eighths of an inch (1.375").

The diverging portion 172 of the nozzle 124 can act as a diffuser that decelerates velocity and increases pressure of the two-phase steam. In one embodiment, the diverging portion 172 can have a six degree (6°) tapered-bore angle. The 6° tapered-bore angle can increase pressure recovery as the two-phase steam enters and exits the nozzle 124. In some instances, the 6° tapered-bore angle can reduce flow separation from the tapered wall, further reducing pressure loss. In some embodiments, an interior of the pipe 126 approximate the nozzle 124 can be machined to extend the taper downstream of the nozzle 124, as shown in FIG. 5.

Generally, the converging/diverging nozzle 124 can mix the two-phase flow in the converging portion 170. In the diverging portion 172, the nozzle 124 can recover energy by tapering outwards at a controlled rate. The outward taper can reduce turbulent flow conditions, which can minimize energy loss. In one embodiment, the nozzle 124 can be a "quiet nozzle," where energy loss is minimized while still mixing the two-phase flow.

In one embodiment, the nozzle 124 can be a positive choke having a fixed orifice and being removably coupled to the pipe 126. As shown in FIG. 5, the nozzle 124 can be located upstream and approximate the electrode 150. Generally, the nozzle 124 can be coupled to an interior of the pipe 126. For instance, the nozzle 124 can be threadably engaged with the pipe 126. In one example, the nozzle 124 can be removably engaged with the pipe 126. It is to be appreciated that a variety means of coupling the nozzle 124 to the pipe 126 can be implemented without exceeding the scope of this disclosure.

In some embodiments, the nozzle 124 can function as a steam flow regulating and control device. By controlling a pressure drop and critical flow conditions, the nozzle 124 can limit flow through the enhanced oil recovery system 100.

A Method of Sizing a Nozzle for a Steam Quality Measurement System

Figure 7:
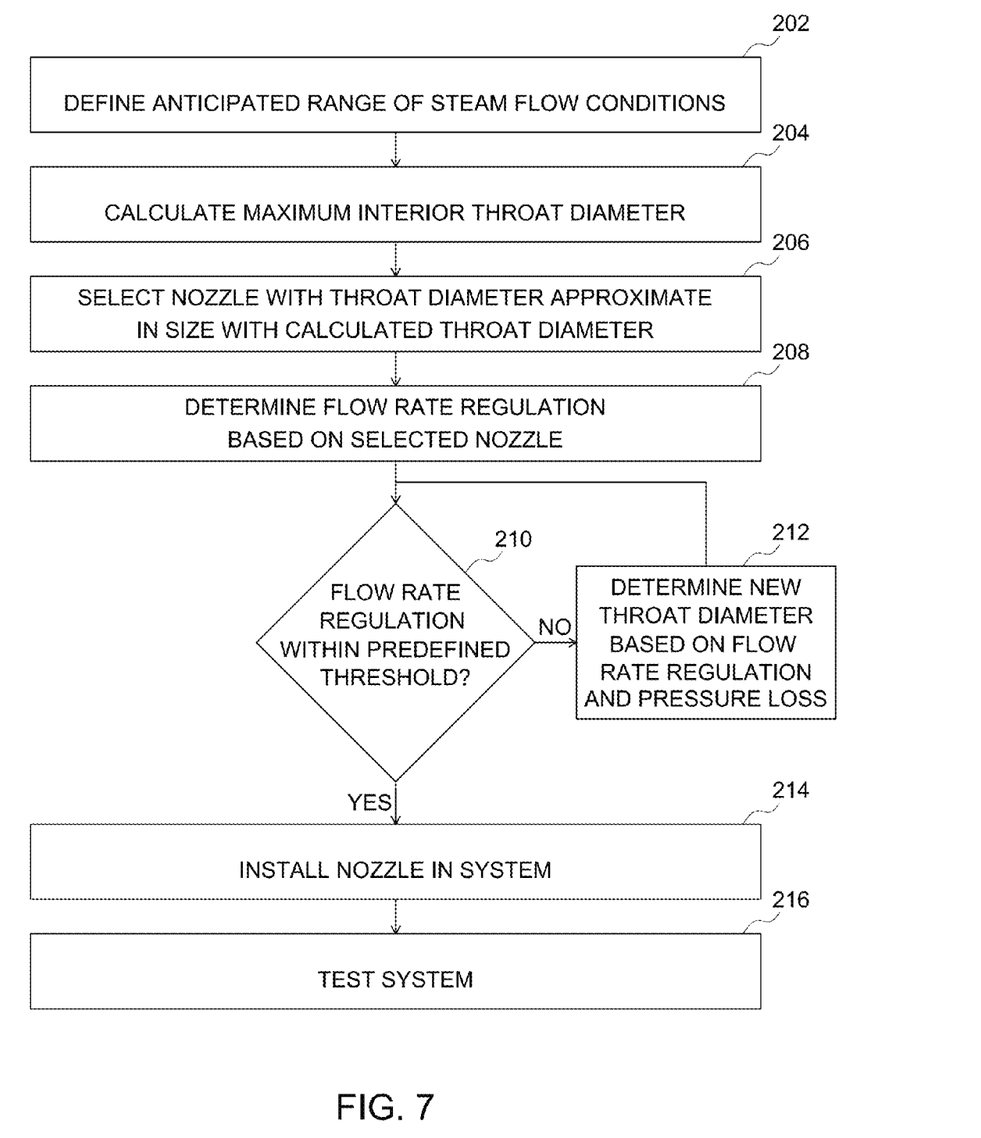
FIG. 7 is a flow diagram illustrating a method according to one embodiment of the present invention.

Referring to FIG. 7, a flow chart illustrating a process 200 for sizing a nozzle for a steam quality measurement system is shown. Depending on a variety of factors, nozzles having different sized throat diameters can be implemented in the steam quality measurement system.

In block 202, an anticipated range of steam flow conditions of an enhanced oil recovery system can be defined. Steam flow conditions can include, but are not limited to, system pressure, steam mass flow rates, and steam quality ranges. Generally, the flow conditions can be defined prior to installation of the steam quality measurement system.

Based on the defined steam flow conditions and producing a mist phase, vapor continuous, zero slip regime, a maximum interior throat diameter of a nozzle can be computed in block 204. In block 206, a nozzle can be selected with a throat diameter approximate in size with the computed throat diameter. Generally, the larger the throat diameter is, the less pressure is lost.

In block 208, flow rate regulation can be determined based on the selected nozzle. Flow rate regulation can be achieved when a velocity of a flow reaches sonic velocity. At sonic velocity, critical flow is achieved which produces a constant flow rate. The process 200 can then move to block 210 to determine if the flow rate is within a predefined threshold. If the flow rate is outside the predefined threshold, the process 200 can move to block 212. If the flow rate is within a predefined threshold, the process 200 can move to block 214.

In block 212, a new throat diameter size can be determined based primarily on flow rate regulation factors and secondarily on pressure loss. For example, increased pressure loss can be traded for better flow rate regulation. The process 200 can move back to block 210 to determine if the flow rate is within the predefined threshold. If the flow rate regulation is acceptable, the system can move to block 214.

In block 214, the nozzle can be installed in the steam quality measurement system. In block 214, live testing of the nozzle and system can be conducted to make sure they are working as predicted.

ALTERNATIVE EMBODIMENTS AND VARIATIONS

The various embodiments and variations thereof, illustrated in the accompanying Figures and/or described above, are merely exemplary and are not meant to limit the scope of the invention. It is to be appreciated that numerous other variations of the invention have been contemplated, as would be obvious to one of ordinary skill in the art, given the benefit of this disclosure. All variations of the invention that read upon appended claims are intended and contemplated to be within the scope of the invention.

I claim:

1. A steam quality measuring device, the device comprising:
    an inlet adapted to receive a two-phase flow;
    a removable nozzle configured to mix the two-phase flow;
    a capacitance measuring sensor, the sensor including an electrically insulating spacer; and
    an outlet located approximate the electrically insulating spacer, the outlet being orthogonally oriented to the electrically insulating spacer.

2. The steam quality measuring device of claim 1, wherein the removable nozzle is a converging/diverging nozzle.

3. The converging/diverging nozzle of claim 2, wherein a converging portion of the nozzle is upstream of a diverging portion of the nozzle.

4. The converging/diverging nozzle of claim 3, wherein a length of the converging portion of the nozzle is shorter than a length of the diverging portion of the nozzle.

5. The converging/diverging nozzle of claim 2, wherein the nozzle is located upstream of the capacitance measuring sensor.

6. The converging/diverging nozzle of claim 2, wherein a pressure drop created by the nozzle is at most 15%.

7. The capacitance measuring sensor of claim 1, wherein the capacitance measuring sensor comprises:
    an electrode,
    the electrically insulating spacer;
    one or more seals; and
    a rod connected to (i) the electrode and (ii) a power source.

8. The steam quality measuring device of claim 1, wherein the device further comprises a pressure release assembly.

9. The steam quality measuring device of claim 1, wherein the two-phase flow comprises water vapor and liquid water.

10. The steam quality measuring device of claim 1, wherein the removable nozzle is four inches in length.

11. The steam quality measuring device of claim 10, wherein the removable nozzle has a throat diameter of 0.375 inches to 1.375 inches.

12. The steam quality measuring device of claim 1, the device further comprising:

a first sensor; and
a second sensor.

13. The steam quality measuring device of claim 12, wherein the first sensor consists of one of:
a temperature sensor; and
a pressure sensor.

14. The steam quality measuring device of claim 12, wherein the second sensor consists of one of:
a temperature sensor; and
a pressure sensor.

15. The steam quality measuring device of claim 12, wherein the first sensor is located upstream of the removable nozzle and the second sensor is located downstream of the removable nozzle.

16. A two-phase flow quality measurement system, the system comprising:
a two-phase flow generator;
a two-phase flow quality measuring device coupled to the two-phase flow generator, wherein the device comprises:
an inlet adapted to receive the two-phase flow;
a removable nozzle configured to mix the two-phase flow;
a capacitance measuring sensor, the sensor including an electrically insulating spacer; and
an outlet located approximate the electrically insulating spacer, the outlet being orthogonally oriented to the electrically insulating spacer;
one or more injectors coupled to the outlet of the two-phase flow quality measuring device.

17. The two-phase flow quality measuring system of claim 16, wherein the removable nozzle comprises a converging/diverging nozzle.

18. The converging/diverging nozzle of claim 17, wherein a converging portion of the nozzle is shorter than a diverging portion of the nozzle.

19. The two-phase flow quality measuring system of claim 16, wherein the two-phase flow quality measuring system further comprises:
a network interface configured to transmit a signal; and
a controller connected to the network interface, wherein the controller is configured to calculate a steam quality and send the steam quality via the network interface.

20. A method for fitting a nozzle to a steam quality measuring device, the method comprising the steps of:
defining a range of steam flow conditions;
calculating a throat diameter based on the range of steam flow conditions;
selecting a nozzle having a throat diameter approximate the calculated throat diameter;
determining flow rate based on the selected nozzle;
installing the selected nozzle in the steam quality measuring device if the determined flow rate is within a defined threshold.

* * * * *